United States Patent [19]

Rothgery

[11] Patent Number: 4,482,738

[45] Date of Patent: Nov. 13, 1984

[54] PROCESS FOR PREPARING SEMICARBAZIDE HYDROCHLORIDE

[75] Inventor: Eugene F. Rothgery, North Branford, Conn.

[73] Assignee: Olin Corporation, Cheshire, Conn.

[21] Appl. No.: 519,471

[22] Filed: Aug. 1, 1983

[51] Int. Cl.$^3$ .......................................... C07C 133/02
[52] U.S. Cl. ....................................... 564/37; 564/18; 564/34; 564/35
[58] Field of Search ....................... 564/18, 34, 35, 37

[56] References Cited

U.S. PATENT DOCUMENTS

| Re. 24,526 | 8/1958 | Sampson, Jr. | 260/554 |
| 2,692,281 | 10/1954 | Newby et al. | 564/35 |
| 2,749,217 | 6/1956 | Deutschman, Jr. | 23/190 |
| 3,227,753 | 1/1966 | Mehr et al. | 564/35 |

FOREIGN PATENT DOCUMENTS 848167  9/1960  United Kingdom ................. 564/37

OTHER PUBLICATIONS

Charles Clark, *Hydrazine*, Mathieson Chemical Corporation, pp. 59-63, (1953).
Mistry et al., J. Ind. Chem. Soc., vol. 7, p. 793, (1930).
Das-Gupta, J. Ind. Chem. Soc., vol. 10, p. 111, (1933).
Wheeler, JACS, 51, 3654, (1929).

*Primary Examiner*—Thomas A. Waltz
*Attorney, Agent, or Firm*—William A. Simons; Thomas P. O'Day

[57] ABSTRACT

A process for preparing semicarbazide hydrochloride comprising the steps:

(a) reacting an aqueous hydrazine solution with urea at a temperature from about 80° C. to about 130° C. and at a mole ratio of hydrazine to urea from about 0.9:1 to about 1.2:1 to form a reaction mixture comprising semicarbazide, water and alcohol-insoluble by-products;

(b) removing substantially all of the water from the reaction mixture;

(c) mixing a sufficient amount of an alcohol with the water-deleted reaction mixture to dissolve the semicarbazide and to precipitate said alcohol-insoluble by-products from the resulting alcohol solution;

(d) removing said precipitated alcohol-insoluble by-products from said alcohol solution;

(e) adding a sufficient amount of anhydrous hydrogen chloride to said alcohol solution to form and precipitate semicarbazide hydrochloride; and (f) recovering said semicarbazide hydrochloride from said alcohol solution.

8 Claims, No Drawings

PROCESS FOR PREPARING SEMICARBAZIDE HYDROCHLORIDE

BACKGROUND OF THE INVENTION

1. Field of the Invention

The present invention relates to a process for preparing semicarbazide hydrochloride.

2. Description of the Prior Art

Semicarbazide hydrochloride is an important hydrazine-based chemical intermediate used in the production of pharmaceuticals, photographic chemicals and other products. This compound has been prepared by a variety of synthesis routes. One preparation method involves reacting carbon monoxide with hydrazine at superatmospheric pressures and at temperatures in the range from 0° C. to 200° C. and in the presence of a catalytic amount of a metal carbonyl to obtain semicarbazide which was acidified to yield the desired salt. See U.S. Pat. Reissue No. 24,526, which reissued to H. J. Sampson, Jr. on Aug. 26, 1958.

Another method involves reacting nitrourea with hydrogen in the presence of a hydrogenation catalyst, hydrochloric acid and an inert solubilizing agent to produce semicarbazide hydrochloride. See U.S. Pat. No. 2,749,217, which issued to A. J. Deutschman, Jr. on June 5, 1956.

A preferred commercial route involves the reaction of hydrazine hydrate (64% by weight hydrazine) with urea. At the end of the reaction, the water and unreacted hydrazine from the hydrazine solution is stripped. The reaction mixture is then digested in methanol followed by filtering off methanol-insoluble by-products (e.g. hydrazodicarbonamide). The remaining filtrate is acidified with aqueous hydrochloric acid to precipitate semicarbazide hydrochloride which is then recovered.

This latter route, while being advantageous in being able to use atmospheric pressure reactions and inexpensive reactants, does have the disadvantage of having relatively low yields (i.e. about 75% to 80% based on the urea used). Accordingly, there is a need in the art to be able to improve the yields of this process without substantially increasing its costs. The present invention is believed to be a solution to that need.

BRIEF SUMMARY OF THE INVENTION

The present invention, therefore, is directed to a process for making semicarbazide hydrochloride comprising the steps of:

(a) reacting an aqueous hydrazine solution with urea at a temperature from about 80° C. to about 130° C. and at a mole ratio of hydrazine to urea from about 0.9:1 to about 1.2:1 to form a reaction mixture comprising semicarbazide, water and alcohol-insoluble by-products;

(b) removing substantially all (i.e. at least about 95% by weight) of the water from the reaction mixture;

(c) mixing a sufficient amount of an alcohol with the water-deleted reaction mixture to dissolve the semicarbazide and to precipitate the alcohol-insoluble by-products from the resulting alcohol solution;

(d) removing the precipitated alcohol-insoluble by-products from the alcohol solution;

(e) adding a sufficient amount of anhydrous hydrogen chloride to the alcohol solution to form and precipitate semicarbazide hydrochloride; and (f) recovering the semicarbazide hydrochloride from the alcohol solution.

DETAILED DESCRIPTION

The formation of semicarbazide hydrochloride from urea, hydrazine and HCl is illustrated by the following equations (A) and (B):

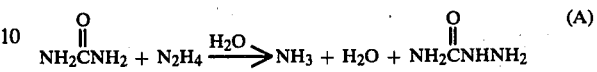

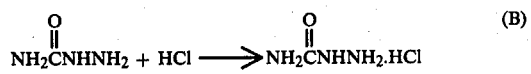

The reactants for this process are widely available chemicals. Urea is a widely available commodity chemical. Hydrazine is also commonly available in the form of hydrazine hydrate (an aqueous solution containing 1 mole hydrazine and 1 mole $H_2O$ or 64% by weight hydrazine). It is also available in other aqueous solutions (e.g. solutions containing from about 95% to about 5% by weight hydrazine). Hydrazine hydrate is the preferred source of hydrazine for this process.

It is critical to the present process to employ anhydrous HCl. It has been found that employment of anhydrous HCl instead of the more commonly available aqueous solutions of HCl significantly increases the product yield. The term "anhydrous HCl" as employed herein includes HCl solutions which contain less than about 2% by weight $H_2O$.

The mole ratio of hydrazine to urea, as stated above, should be from about 0.9:1 to about 1.2:1. The employment of this range of mole ratios is important because low yields of product would be obtained if a siginificant excess of hydrazine was employed and the formation of the by-product, hydrazodicarbonamide, is favored with significant excess of urea. It is more preferred to employ a hydrazine to urea mole ratio from about 0.95:1 to about 1.1:1.

The reaction temperature should be from about 80° C. to about 130° C. in order to achieve the reasonable reaction rate. The reaction rate appears to slow down significantly below about 80° C. Above about 130° C., degradation reactions are initiated which lower the product yield and complicates its recovery. Preferably the reaction should be carried out to about 100° C. to about 120° C. The reaction time is dependent upon the reaction temperature and with higher temperatures a shorter time would be needed. The present invention does not require the use of either sub- or superatmospheric pressures during the reaction. It is preferred to use atmospheric pressure reactors of conventional construction. It should be noted that ammonia is evolved as a by-product during the reaction and minute amounts of ammonia may be still present at the end of the reaction. However, these may usually be removed with the water.

After the reaction is complete, it is necessary to remove substantially all of the water in the reaction mixture which originated with the aqueous hydrazine solution. This water removal step can be carried out by any conventional means. Vacuum distillation is the preferred technique for removing water. Excess hydrazine and ammonia will also be removed by this step. In a preferred embodiment, at least about 98% by weight of the $H_2O$ is removed by this step.

Upon completion of the water removal step the water-deleted residue (i.e. containing semicarbazide and alcohol-insoluble by-products such as hydrazodicarbonamide) is mixed with an alcohol to preferentially dissolve substantially all of the semicarbazide and precipitate substantially all of the alcohol-insoluble by-products. Any of the lower alcohols having 1–4 carbon atoms such as methanol ethanol, isopropanol and the like are preferred. It is more preferred to use methanol because of the higher solubility of semicarbazide in it. It may also be preferable to heat this mixture (e.g. to about 55° C. to about 65° C.) in order to achieve greater solubility of the semicarbazide. Also the mixture may be agitated for the same purpose. The preferred amount of alcohol added is at least equal by weight to the amount of the water-deleted reaction mixture.

When the alcohol-insolubles are completely settled or precipitated from the solution, they may be removed by any conventional means. Filtration is preferred although other conventional techniques, such as centrifugation and the like, may be used instead.

After separation of the insolubles, the clarified alcoholic mixture is acidified with anhydrous HCl to form the desired semicarbazide hydrochloride product. The preferred amount of HCl added should be approximately a 1:1 mole ratio with the semicarbazide. Preferably, the anhydrous acid is added slowly into the alcoholic mixture. This addition of the HCl forms a precipitate which is the desired product.

The precipitated semicarbazide hydrochloride may be recovered from the alcoholic mixture by any conventional means. Again filtration is the preferred technique although other conventional techniques may be used. After removal of the alcoholic mixture from the product, the product may be washed in methanol and dried for use in other processes.

The following example and comparison further illustrate the present invention. All parts and percentages are by weight unless explicity stated otherwise.

EXAMPLE I

Use of Anhydrous Acid Conditions

Urea (60.1 g, 1 mole) and 64% aqueous hydrazine solution (55 g, 1.10 moles) were placed in a 250 ml, 3-neck flask and heated at reflux (115°–120° C.) for three hours evolving gaseous ammonia. At the end of the reaction period, the excess hydrazine and accompanying water were vacuum stripped at 70° C. and 10 torr, leaving semicarbazide and by-products including hydrazodicarbonamide. These were separated by digesting in 200 ml of boiling methanol for 45 minutes and filtering off the insoluble hydrazodicarbonamide (5.5 g). The filtrate was cooled to 10° C. and a solution of 37 g (one mole) of anhydrous hydrogen chloride in 65 ml of methanol added. The product precipitated, was filtered off, washed with 50 ml of methanol and dried to give 100 g of semicarbazide hydrochloride—89.7% of theory based on urea charged and assaying 97.6% by NaOH titration.

Comparison I

Use Of Aqueous Acid Conditions

Urea and 64% hydrazine were reacted on the same scale and conditions as in Example I, except that after digesting the mixture and filtering away the hydrazodicarbonamide, 98 g of 37% aqueous hydrochloric acid (1 mole) was added to precipitate the semicarbazide hydrochloride. The product was filtered from the methanol/water solution, washed with methanol and dried to give 86.2 g, which represents 77.3% of theory based on urea charged and assaying 97.8% pure by NaOH titration.

Comparing the product yield of Example I to Comparison I, one can readily see that the process of the present invention produces a significantly higher yield.

What is claimed is:

1. A process for making semicarbazide hydrochloride comprising the steps of:
    (a) reacting an aqueous hydrazine solution with urea at a temperature from about 80° C. to about 130° C. and at a mole ratio of hydrazine to urea from about 0.9:1 to about 1.2:1 to form a reaction mixture comprising semicarbazide, water and alcohol-insoluble by-products;
    (b) removing substantially all of the water from the reaction mixture;
    (c) mixing a sufficient amount of an alcohol with the water-deleted reaction mixture to dissolve said semicarbazide and to precipitate said alcohol-insoluble by-products from the resulting alcohol solution;
    (d) removing said precipitated alcohol-insoluble by-products from said alcohol solution;
    (e) adding a sufficient amount of anhydrous hydrogen chloride to said alcohol solution to form and precipitate semicarbazide hydrochloride; and
    (f) recovering said semicarbazide hydrochloride from said alcohol solution.

2. The process of claim 1 wherein said aqueous hydrazine solution is hydrazine hydrate.

3. The process of claim 1 wherein the reaction temperature for step (a) is from about 105° C. to about 120° C.

4. The process of claim 1 wherein the mole ratio of hydrazine to urea is from about 0.95:1 to about 1.1:1.

5. The process of claim 1 wherein said alcohol is a lower alcohol having 1 to 4 carbon atoms.

6. The process of claim 5 wherein said lower alcohol is methanol.

7. The process of claim 1 wherein the amount of hydrogen chloride added in step (e) is approximately an equal molar amount to the semicarbazide present in said alcohol solution.

8. A process for making semicarbazide hydrochloride comprising the steps of:
    (a) reacting hydrazine hydrate with urea at a temperature from about 100° C. to about 120° C. and at a mole ratio of hydrazine to urea from about 0.95:1 to about 1.1:1 to form a reaction mixture comprising semicarbazide, water and methanol-insoluble by-products;
    (b) removing substantially all of the water from the reaction mixture;
    (c) mixing a sufficient amount of methanol with the water-deleted reaction mixture to dissolve said semicarbazide and to precipitate said methanol-insoluble by-products from the resulting methanol solution;
    (d) filtering said precipitated methanol-insoluble by-products from said methanol solution;
    (e) adding anhydrous hydrogen chloride to said methanol solution to form and precipitate semicarbazide hydrochloride, the amount of said hydrogen chloride added being approximately an equal molar amount to the semicarbazide present in the methanol solution; and
    (f) filtering said semicarbazide hydrochloride from said methanol solution.

* * * * *